United States Patent [19]
Frankenreiter

[11] Patent Number: 5,427,109
[45] Date of Patent: Jun. 27, 1995

[54] METHOD AND APPARATUS FOR AUTOMATIC NON-INVASIVE MONITORING OF A PATIENT'S BLOOD PRESSURE

[75] Inventor: Michael Frankenreiter, Sindelfingen, Germany

[73] Assignee: Hewlett-Packard Company, Palo Alto, Calif.

[21] Appl. No.: 208,448

[22] Filed: Mar. 9, 1994

Related U.S. Application Data

[63] Continuation-in-part of Ser. No. 6,240, Jan. 19, 1993, abandoned.

[51] Int. Cl.⁶ .................................................. A61B 5/00
[52] U.S. Cl. ........................................ 128/680; 128/681; 128/682
[58] Field of Search ........................... 128/677–683; 364/413.03

[56] References Cited

U.S. PATENT DOCUMENTS

| | | | |
|---|---|---|---|
| 4,461,266 | 7/1984 | Hood, Jr. et al. | 128/680 |
| 4,534,361 | 8/1982 | Berger et al. | 128/680 |
| 4,592,365 | 6/1986 | Georgi | 128/680 |
| 4,735,213 | 4/1988 | Shirasaki | 128/681 |
| 4,796,184 | 1/1989 | Bahr et al. | 128/681 |
| 5,105,354 | 4/1992 | Nishimura | 364/413.03 |
| 5,203,341 | 4/1993 | Souma | 128/680 |
| 5,215,096 | 6/1993 | Zapf et al. | 128/682 |
| 5,253,648 | 10/1993 | Walloch | 128/681 |

Primary Examiner—Lee S. Cohen
Assistant Examiner—Robert L. Nasser, Jr.

[57] ABSTRACT

In a method for automatic non-invasive monitoring of a patient's blood pressure a cuff is applied around an arm of the patient and inflated to a predetermined pressure, whereafter the pressure in said cuff is stepwise reduced and the applied pressure is held constant at each step until at least one oscillation caused by a heartbeat has occurred. In such a method, the systolic and/or diastolic and/or mean blood pressure are determined on the basis of the relations of the amplitudes or peak values of the oscillations at the various pressure steps. In order to avoid errors in the blood pressure determination due to artifacts, a first aspect of the invention provides for a spectral analyzer for pressure signal frequencies between 6 and 10 Hz. When this analyzer detects spectral signal components of the pressure signal in the pressure channel above a specific amplitude limit, the instantaneous oscillation is rejected. According to a second aspect of the invention, the gradient and the scatter of the pressure channel signal are examined within a time window, and, in case one of the two limit values for said ascent or scattering are exceeded, a movement artifact is detected.

25 Claims, 3 Drawing Sheets

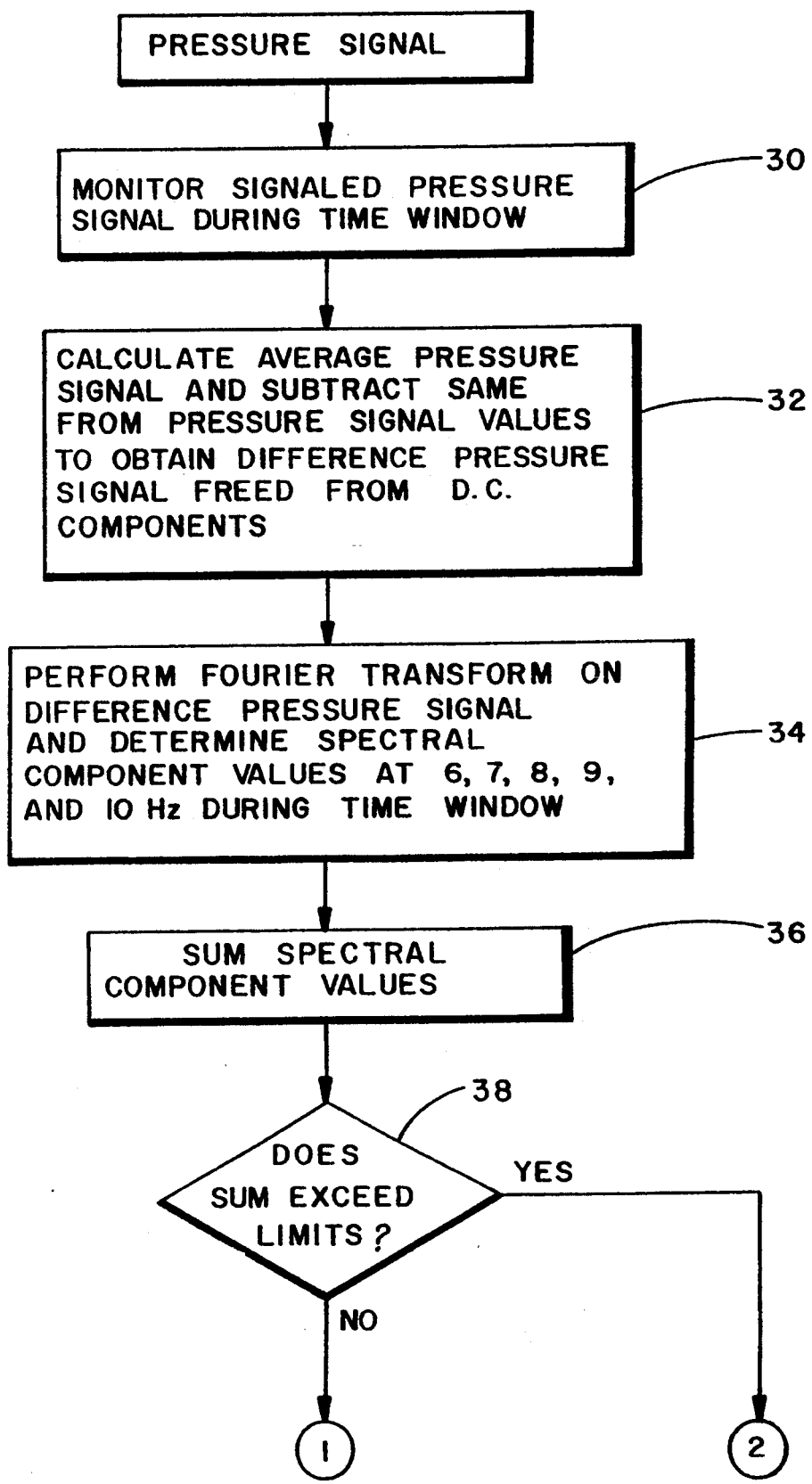

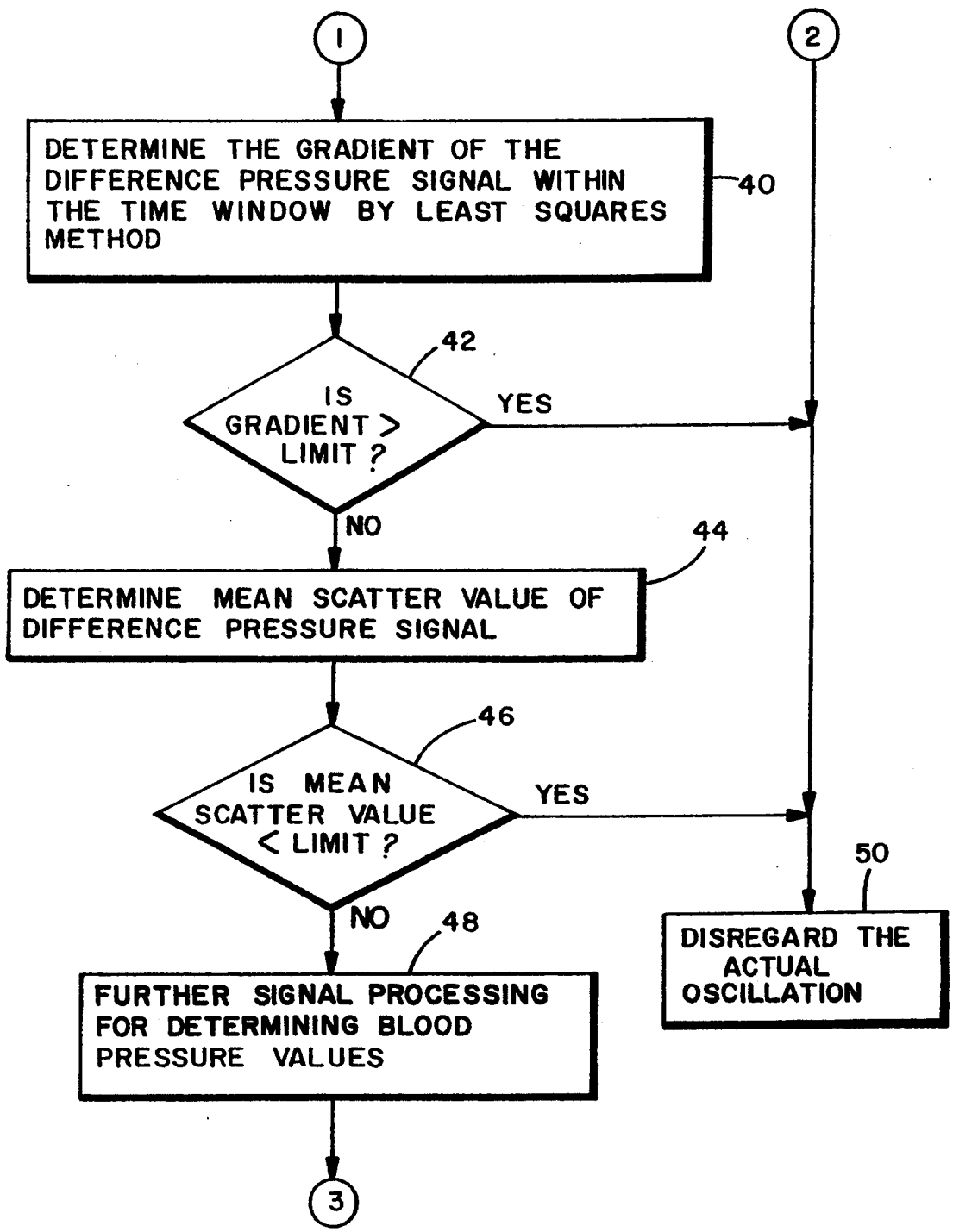

METHOD AND APPARATUS FOR AUTOMATIC NON-INVASIVE MONITORING OF A PATIENT'S BLOOD PRESSURE

This is a continuation-in-part of application Ser. No. 08/006,240 filed on Jan. 19, 1993, now abandoned.

FIELD OF THE INVENTION

The present invention relates in general to automatic noninvasive monitoring of a patient's blood pressure. In accordance with a major aspect, the invention relates to a method for automatic noninvasive monitoring of a patient's blood pressure, comprising the steps of applying a cuff around an arm of the patient, inflating said cuff to a predetermined pressure, generating a pressure signal by means of a pressure sensor, stepwise reducing the pressure applied to said cuff for instance by opening a controllable valve, with the applied pressure being held constant at each step until at least one oscillation caused by a heartbeat has occurred in said pressure signal or until a predetermined time period has expired starting as of holding the applied pressure constant, and the systolic or the diastolic or the mean blood pressure being derived from the amplitudes of the oscillations at the various pressure steps.

CROSS REFERENCE TO RELATED APPLICATION (1) U.S. patent application, Ser. No. 08/208,477, Entitled: "METHOD AND APPARATUS FOR AUTOMATIC NON-INVASIVE MONITORING OF A PATIENT'S BLOOD PRESSURE", Frankenreiter, M (2) U.S. patent application, Ser. No. 08/208,444, Entitled: "METHOD AND APPARATUS FOR AUTOMATIC NON-INVASIVE MONITORING OF A PATIENT'S BLOOD PRESSURE", Frankenreiter and Gobl

DESCRIPTION OF THE PRIOR ART

In a manual method of measuring a patient's blood pressure in non-invasive manner, a cuff is applied to an arm of the patient and pumped up to a blood pressure above the systolic blood pressure of the patient. The arteries of the patient are thereby pressed together in occluding manner. The cuff pressure is then continuously decreased while the physician or the nurse monitors by means of a stethoscope the start and the end of the opening of the arteries in order to determine on the basis of these so-called Korotkoff sounds the upper, systolic and the lower, diastolic blood pressure by simultaneously reading these values off from a manometer.

There are also automatic methods for performing this measurement, called "auscultation technique". The blood pressure monitors employing this technique are not deemed reliable.

Blood pressure monitors and blood pressure measuring methods, respectively, have been employed for a number of years in which the so-called oscillometric method is utilized which uses the oscillations or fluctuations of the walls of the arteries which occur in synchronism with the blood pulse. According to the oscillometric technique, the cuff is pumped up to a pressure beyond the systolic pressure and is then deflated in discrete steps. Alternatively, the cuff is inflated in discrete pressure steps up to a predetermined measure beyond the systolic pressure.

During each step, where the cuff pressure is held substantially constant, a pressure sensor detects the oscillations caused by movement of the arterial walls and superimposed on the constant cuff pressure. The amplitudes of these oscillations are recorded. The oscillations, at the systolic or diastolic pressure, respectively, have an amplitude value or peak-to-peak value that is a fixed percentage of the maximum amplitude or maximum peak-to-peak value at mean pressure. Thus, in the oscillometric measuring method the pressure determined as systolic or diastolic pressure generally is the pressure at which the amplitude or peak-to-peak value of the oscillations is a specific percentage of the maximum amplitude of the oscillations.

Blood pressure monitors employing the aforedescribed oscillometric technique have been known for some time so that it is sufficient for disclosing details of this measurement technique to make reference to the following publications as prior art: U.S. Pat. No. 4,349,034, EP-A-208520, EP-A-353315, EP-A-353316, and U.S. Pat. No. 4,074,711.

U.S. Pat. No. 4,625,277, EP-A-249243 and EP-A-379996 disclose methods and apparatuses for the automative non-invasive monitoring of a patient's blood pressure which do not inflate or deflate the cuff in discrete pressure steps. Rather, in accordance with these prior art methods, the cuff is either continuously inflated to a predetermined pressure while taking the number of pressure signal examples during the course of the continuous inflation of the cuff to then deflate the cuff after having reached the predetermined pressure value, or the cuff is rapidly inflated to the predetermined pressure value and then continuously deflated while taking the pressure signal samples during the course of the continuous deflating of the cuff from the above pressure. Thus, the above-described oscillometric measuring method for determining a patient's blood pressure can be used in both cases, in case of a method taking samples of the pressure signal when holding the applied pressure constant until a heartbeat has occurred, as well as in case of a method taking samples of the pressure signal during the course of the continuously inflating or deflating of the cuff.

However, the pressure signal obtained for example by means of a pressure sensor in the cuff on the patient's arm is not only determined by the static cuff pressure and the described oscillations which are determined by oscillations of the arterial walls due to the blood pressure. In other words, the pressure signal has various disturbance variables superimposed thereon that may have different causes. Typical disturbances superimposed on the pressure signal are movements of the patient and muscular tremor occurring in particular in case of undercooling of the patient. In addition thereto there are physiological peculiarities, including all kinds of arrhythmia, such as for instance bigeminy and trigeminy, as well as the so-called respiratory superimposition, i.e. the superimposition of a signal component caused by the patient's breathing on the useful signal. While movements and muscular tremor must be separated from the measuring signal proper, arrhythmias and respiratory superimpositions are signals to be taken into consideration in the measurement.

It is known in oscillometric blood pressure monitors to disregard such oscillations for determining the blood pressure value which are recognized to have been caused by an artifact or have an artifact superimposed thereon. An artifact in known blood pressure monitors is recognized on the basis of a criterion derived from the so-called oscillation channel. In oscillometric blood pressure monitors, the oscillation channel is understood to be a signal channel obtained on the basis of the so-called pressure channel signal, which constitutes the pressure sensor output, by high-pass filtering. This oscillation channel thus corresponds to the harmonic waves or oscillations superimposed on the pressure channel, disregarding the constant component. This oscillation channel signal is rejected as having an artifact superimposed thereon when either the ascending slope of an oscillation exceeds a maximum increase value or when, at a pressure step, the amplitude difference of two adjacent oscillations exceeds a maximum value or when an envelope criterion is not fulfilled according to which an examination is made as to whether two oscillation amplitudes have not become more than double or less than half between two adjacent steps or when the time interval between two oscillations varies by more than a specific percentage of the average time interval. This examination in the prior art, which is carried out on the basis of the oscillation channel, is not capable of making a distinction whether one of the artifact examination criteria has shown responsive because an artifact was actually present or because an arrhythmia or respiratory superimposition of a greater extent has occurred.

Because of the susceptibility of the algorithm used in the known oscillometric blood pressure monitor, both erroneous measurements and unnecessary alarms occur. This is of significance in particular since such blood pressure monitors are often employed in operating rooms where a multiplicity of other parameters of a patient must also be monitored, which may all cause alarms. Such medical apparatus must therefore keep the number of false alarms as low as possible, however without risking the recognition of a genuine physiological alarm.

SUMMARY OF THE INVENTION

It is thus a major object of the present invention to provide a method for automatic non-invasive monitoring of a patient's blood pressure as well as an apparatus therefor in which artifacts, in particular based on muscular tremor of the patient, do not result in errors in determining the systolic or the diastolic or the mean blood pressure.

In accordance with a first aspect of the invention, this object is met by a method for automatic non-invasive monitoring of a patient's blood pressure, comprising the following steps:
applying a cuff around an arm of the patient,
inflating said cuff to a predetermined pressure,
generating a pressure signal,
stepwise reducing the pressure applied to said cuff,
holding the applied pressure constant at each step until
 at least one oscillation caused by a heartbeat has occurred in said pressure signal, or until
 a predetermined time period has expired,
determining at least one spectral component of the pressure signal in the frequency range between 6 and 10 Hz,
examining whether the amplitude of the spectral component exceeds a limit value, and
 if yes, disregarding the instantaneous oscillation of the pressure signal in further processing of said signal; or
 if this condition is not fulfilled, processing the oscillation for determining either the systolic or the diastolic or the mean blood pressure.

In accordance with a second aspect of the invention, this object is met by a method for automatic non-invasive monitoring of a patient's blood pressure, comprising the following steps:
applying a cuff around an arm of the patient,
stepwise inflating said cuff to a predetermined pressure and holding the applied pressure constant at each step until
 at least one oscillation caused by a heartbeat has occurred in said pressure signal, or until
 a predetermined time period has expired,
generating a pressure signal,
determining at least one spectral component of the pressure signal in the frequency range between 6 and 10 Hz,
examining whether the amplitude of the spectral component exceeds a limit value, and
 if this condition is fulfilled, disregarding the instantaneous oscillation of the pressure signal in further processing of said signal; or
 if this condition is not fulfilled, processing the oscillation for determining either the systolic or the diastolic or the mean blood pressure,
after having reached the predetermined pressure, deflating said cuff.

In accordance with a third aspect of the invention, this object is met by a method for automatic non-invasive monitoring of a patient's blood pressure, comprising the following steps:
applying a cuff around an arm of the patient,
continuously inflating said cuff to a predetermined pressure or continuously deflating said cuff from a predetermined pressure,
generating a pressure signal during the course of the continuous inflating said cuff to said predetermined pressure or during the course of the continuous deflating said cuff from said predetermined pressure,
determining at least one spectral component of the pressure signal in the frequency range between 6 and 10 Hz,
examining whether the amplitude of the spectral component exceeds a limit value, and
 if this condition is fulfilled, disregarding the instantaneous oscillation of the pressure signal in further processing of said signal; or
 if this condition is not fulfilled, processing the oscillation for determining either the systolic or the diastolic or the mean blood pressure.

Further, this object is met in accordance with a fourth aspect of the invention by a blood pressure measuring apparatus for automatic noninvasive monitoring of a patient's blood pressure, comprising:
a cuff applied to an arm of the patient,
pump means for inflating said cuff to a predetermined pressure,
a pressure sensor for producing a pressure signal,
valve means coupled to said cuff for stepwise reducing the pressure applied to said cuff and for holding the applied pressure constant at each step until
 at least one oscillation caused by a heartbeat has occurred in the pressure signal, or until
 a predetermined period of time has expired, a spectral component determining means for determining at least one spectral component of the pressure signal in the frequency range between 6 and 10 Hz, an examination means for examining whether the amplitude of the spectral component exceeds a limit value, and if this condition is fulfilled, disregarding the instantaneous oscillation of the pressure signal in further processing of said signal; or if this condition is not fulfilled, processing the oscillation for determining either the systolic or the diastolic or the mean blood pressure.

Further, this object is met in accordance with a fifth aspect of the invention by a blood pressure measuring apparatus for automatic noninvasive monitoring of a patient's blood pressure, comprising:

a cuff applied to an arm of the patient, a pressure sensor for producing a pressure signal, a pump means for stepwise inflating said cuff to a predetermined pressure and for holding the applied pressure constant at each step until at least one oscillation caused by a heartbeat has occurred in the pressure signal, or until a predetermined period of time has expired, a spectral component determining means for determining at least one spectral component of the pressure signal in the frequency range between 6 and 10 Hz, an examination means for examining whether the amplitude of the spectral component exceeds a limit value, and if this condition is fulfilled, disregarding the instantaneous oscillation of the pressure signal in further processing of said signal; or if this condition is not fulfilled, processing the oscillation for determining either the systolic or the diastolic or the mean blood pressure, valve means for deflating said cuff when the pressure applied to the cuff has reached the predetermined pressure.

Further, this object is met in accordance with a sixth aspect of the invention by a blood pressure measuring apparatus for automatic noninvasive monitoring of a patient's blood pressure, comprising:

a cuff applied to an arm of the patient, a pump means for continuously inflating said cuff to a predetermined pressure, a pressure sensor for producing a pressure signal during the course of continuously inflating said cuff to said predetermined pressure, a spectral component determining means for determining at least one spectral component of the pressure signal in the frequency range between 6 and 10 Hz, an examination means for examining whether the amplitude of the spectral component exceeds a limit value, and if this condition is fulfilled, disregarding the instantaneous oscillation of the pressure signal in further processing of said signal; or if this condition is not fulfilled, processing the oscillation for determining either the systolic or the diastolic or the mean blood pressure, and valve means for deflating said cuff when the pressure applied to the cuff has reached the predetermined pressure.

Further, this object is met in accordance with a seventh aspect of the invention by a blood pressure measuring apparatus for automatic noninvasive monitoring of a patient's blood pressure, comprising:

a cuff applied to an arm of the patient, a pump means for inflating said cuff to a predetermined pressure, valve means for continuously deflating said cuff from said predetermined pressure, a pressure sensor for producing a pressure signal during the course of continuously deflating said cuff from said predetermined pressure, a spectral component determining means for determining at least one spectral component of the pressure signal in the frequency range between 6 and 10 Hz, an examination means for examining whether the amplitude of the spectral component exceeds a limit value, and if this condition is fulfilled, disregarding the instantaneous oscillation of the pressure signal in further processing of said signal; or if this condition is not fulfilled, processing the oscillation for determining either the systolic or the diastolic or the mean blood pressure.

A new finding of the invention resides in that the patient's tremor contains distinct frequency components in the range between 6 and 10 Hz. By ascertaining the spectral components of the pressure signal in the frequency range between 6 and 10 Hz and examining whether the amplitudes of these spectral components exceed a limit value, it is possible to reliably reject such signals which are impaired by muscular tremor of the patient.

According to an important aspect of the invention, the determination of the spectral components of the pressure signal in the afore-mentioned frequency range between 6 and 10 Hz is made on the basis of a pressure channel signal produced by the pressure sensor and containing also constant components in addition to the oscillation components. This constitutes an essential difference from the technique used so far, which utilized solely an oscillation channel signal obtained from the pressure channel signal by high-pass filtering for judging whether the signals are free from interferences or disturbances.

In an advantageous solution according to the invention, processing of the oscillations for determining the systolic or the diastolic or the mean blood pressure nevertheless takes place on the basis of the oscillation channel signal obtained by high-pass filtering of the pressure channel signal.

Although it is possible according to the invention to employ a band pass filter for determining the spectral components in the frequency range between 6 and 10 Hz, the spectral components according to an advantageous approach of the invention are obtained by a discrete Fourier transform of a pressure signal in the frequency range between 6 and 10 Hz, typically employing a time window of the pressure channel of between 0.2 and 5 seconds, preferably 1 second.

A further major object of the present invention resides in providing a method for automatic non-invasive monitoring of a patient's blood pressure as well as a blood pressure measuring apparatus of the oscillometric type, in which an artifact based on a movement of the patient does not result in an erroneous determination of the systolic or diastolic or mean blood pressure.

In accordance with a eighth aspect of the invention, this object is met by a method for automatic non-invasive monitoring of a patient's blood pressure, comprising the following steps:

applying a cuff around an arm of the patient, inflating said cuff to a predetermined pressure,
generating a pressure signal,
stepwise reducing the pressure applied to said cuff,
holding the applied pressure constant at each step until
- at least one oscillation caused by a heartbeat has occurred in said pressure signal, or until
- a predetermined time period has expired, producing a time window,
determining the ascent of the pressure signal within the time window,
determining the scattering of the pressure signal within the time window,
examining whether the ascent and/or the scattering exceed predetermined limit values, and
- if this condition is fulfilled, disregarding the instantaneous oscillation of the pressure signal in further processing thereof,
- if this condition is not fulfilled, processing the oscillations for determining either the systolic or the diastolic or the mean blood pressure.

In accordance with a ninth aspect of the invention, this object is met by a method for automatic non-invasive monitoring of a patient's blood pressure, comprising the following steps:
applying a cuff around an arm of the patient,
stepwise inflating said cuff to a predetermined pressure,
generating a pressure signal,
holding the applied pressure constant at each step until
- at least one oscillation caused by a heartbeat has occurred in said pressure signal, or until
- a predetermined time period has expired, producing a time window,
determining the ascent of the pressure signal within the time window,
determining the scattering of the pressure signal within the time window,
examining whether the ascent and/or the scattering exceed predetermined limit values, and
- if this condition is fulfilled, disregarding the instantaneous oscillation of the pressure signal in further processing thereof,
- if this condition is not fulfilled, processing the oscillations for determining either the systolic or the diastolic or the mean blood pressure, and after having reached the predetermined pressure, deflating said cuff.

In accordance with a tenth aspect of the invention, this object is met by a method for automatic non-invasive monitoring of a patient's blood pressure, comprising the following steps:
applying a cuff around an arm of the patient,
continuously inflating said cuff to a predetermined pressure or continuously deflating said cuff from a predetermined pressure,
generating a pressure signal during the course of continuously inflating said cuff to said predetermined pressure or during the course of continuously deflating said cuff from said predetermined pressure,
producing a time window,
determining the ascent of the pressure signal within the time window,
determining the scattering of the pressure signal within the time window,
examining whether the ascent and/or the scattering exceed predetermined limit values, and
- if this condition is fulfilled, disregarding the instantaneous oscillation of the pressure signal in further processing thereof,
- if this condition is not fulfilled, processing the oscillations for determining either the systolic or the diastolic or the mean blood pressure.

Further, this object is met in accordance with a eleventh aspect of the invention by a blood pressure measuring apparatus for automatic noninvasive monitoring of a patient's blood pressure, comprising:
a cuff applied to an arm of the patient,
a pump means for inflating said cuff to a predetermined pressure,
a pressure sensor for producing a pressure signal,
valve means coupled to said cuff for stepwise reducing the pressure applied to said cuff and for holding the applied pressure constant at each step until
- at least one oscillation caused by a heartbeat has occurred in the pressure signal, or until
- a predetermined period of time has expired, a timer device for producing a time window,
a means for determining the ascent of the pressure signal within the time window,
a means for determining the scattering of the pressure signal within the time window,
an examination means for examining whether the ascent and/or the scattering exceed predetermined limit values, and
- if this condition is fulfilled, disregarding the instantaneous oscillation of the pressure signal in further processing thereof,
- if this condition is not fulfilled, processing the oscillations for determining either the systolic or the diastolic or the mean blood pressure.

Further, this object is met in accordance with a twelfth aspect of the invention by a blood pressure measuring apparatus for automatic noninvasive monitoring of a patient's blood pressure, comprising:
a cuff applied to an arm of the patient,
a pressure sensor for producing a pressure signal,
a pump means for stepwise inflating said cuff to a predetermined pressure and for holding the applied pressure constant at each step until
- at least one oscillation caused by a heartbeat has occurred in the pressure signal, or until
- a predetermined period of time has expired, a timer device for producing a time window,
a means for determining the ascent of the pressure signal within the time window,
a means for determining the scattering of the pressure signal within the time window,
an examination means for examining whether the ascent and/or the scattering exceed predetermined limit values, and
- if this condition is fulfilled, disregarding the instantaneous oscillation of the pressure signal in further processing thereof,
- if this condition is not fulfilled, processing the oscillations for determining either the systolic or the diastolic or the mean blood pressure, valve means for deflating said cuff when the pressure applied to the cuff has reached the predetermined pressure.

Further, this object is met in accordance with a thirteenth aspect of the invention by a blood pressure measuring apparatus for automatic noninvasive monitoring of a patient's blood pressure, comprising:
a cuff applied to an arm of the patient,
a pump means for continuously inflating said cuff to a predetermined pressure, a pressure sensor for producing a pressure signal during the course of continuously inflating said cuff to said predetermined pressure, a timer device for producing a time window, a means for determining the ascent of the pressure signal within the time window, a means for determining the scattering of the pressure signal within the time window, an examination means for examining whether the ascent and/or the scattering exceed predetermined limit values, and if this condition is fulfilled, disregarding the instantaneous oscillation of the pressure signal in further processing thereof, if this condition is not fulfilled, processing the oscillations for determining either the systolic or the diastolic or the mean blood pressure, and valve means for deflating said cuff when the pressure applied to the cuff has reached the predetermined pressure.

Further, this object is met in accordance with a fourteenth aspect of the invention by a blood pressure measuring apparatus for automatic noninvasive monitoring of a patient's blood pressure, comprising:

a cuff applied to an arm of the patient, a pump means for inflating said cuff to a predetermined pressure, valve means for continuously deflating said cuff from said predetermined pressure, a pressure sensor for producing a pressure signal during the course of continuously deflating said cuff from said predetermined pressure, a timer device for producing a time window, a means for determining the ascent of the pressure signal within the time window, a means for determining the scattering of the pressure signal within the time window, an examination means for examining whether the ascent and/or the scattering exceed predetermined limit values, and if this condition is fulfilled, disregarding the instantaneous oscillation of the pressure signal in further processing thereof, if this condition is not fulfilled, processing the oscillations for determining either the systolic or the diastolic or the mean blood pressure.

According to this solution aspect of the invention, the movement artifacts are recognized in that a signal preferably derived from the pressure channel is observed during a time window produced by a timer means. The ascent of the pressure signal and the scattering thereof are determined within the time window. A movement artifact is recognized when the thus determined ascent and/or the thus determined scattering exceed predetermined limit values. In this case, the instantaneous oscillation of the pressure signal is disregarded in further processing. If the limit values for the ascent and the scattering are not exceeded, the corresponding oscillations are utilized in processing for determining the systolic or the diastolic or the mean blood pressure.

It is to be noted that processing of the oscillations which are thus freed from oscillations can be made using techniques known per se, as described with respect to the oscillometric blood pressure measurement technique in the initially cited patent specifications. In particular, as elucidated hereinbefore, the systolic or the diastolic blood pressure may be defined as those pressure values at which the oscillation—which is artifact-free due to the measures according to the invention—has a predetermined percentage of the maximum amplitude value or peak-to-peak value of the oscillations at mean blood pressure.

DESCRIPTION OF THE DRAWINGS

FIG. 2 is a high level logic flow diagram illustrating a first part of the method performed by the system of FIG. 1.

FIG. 3 is a high level logic flow diagram illustrating a second part of the method performed by the system of FIG. 1.

DESCRIPTION OF PREFERRED EMBODIMENTS OF THE INVENTION

Figure 1:
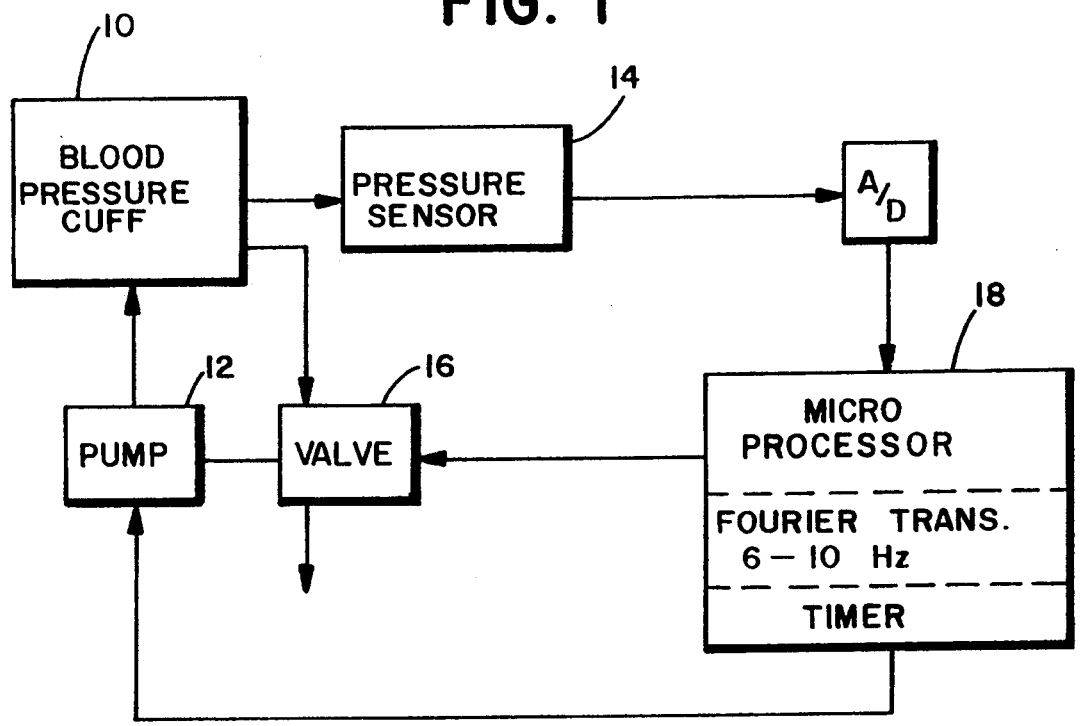
FIG. 1 is a block diagram of a blood pressure measuring system embodying the invention.

The blood pressure measurement apparatus for automatic non-invasive monitoring of a patient's blood pressure is shown in FIG. 1 and comprises a cuff 10 applied to an arm of the patient, a pump 12 for inflating cuff 10 to a predetermined pressure a pressure sensor 14 for producing a pressure signal, a valve means 16 driven by a microprocessor 18 for stepwise reducing the pressure applied to cuff 10 and for holding the applied pressure constant at each step until either at least one oscillation caused by a heartbeat has occurred in the pressure signal or until a predetermined period of time has expired. Microprocessor 18 determines the systolic or the diastolic or the mean blood pressure on the basis of the amplitude relationships of oscillations at the various pressure steps. Preferably, the systolic and the diastolic blood pressure is determined to be the pressure at which the peak-to-peak value of the oscillation reaches a predetermined percentage (e.g. 60%), of the maximum peak-to-peak value at mean blood pressure.

Referring to the flow diagram shown in FIG. 2, the pressure channel signal (i.e. the signal produced by the pressure sensor which is not high-pass filtered), is monitored during a time window (box 30). The average pressure value is then calculated and subtracted from the pressure signal value to obtain difference pressure values free of any dc or constant pressure component (box 32). The difference pressure values are then subjected to a discrete Fourier transform in the range between 6 and 10 Hz (box 34). Preferably, the values of the discrete frequency components at 6, 7, 8, 9 and 10 Hz are determined.

This discrete Fourier transform turns out to be particularly simple when values (sine/cosine) multiplied by a factor 100 are stored before as integers in a table of the microprocessor. The pressure signal is determined for the discrete Fourier transform within a time window between 0.2 and 5 seconds, preferably within a time window of 1 second, with the average value of the signal across the time window being deducted from the signal to achieve the difference pressure signal (box 32) before the discrete Fourier transform is carried out. The values of the spectral components of the signal at the frequencies of 6 Hz, 7 Hz, 8 Hz, 9 Hz and 10 Hz are added (box 36). The total sum of the frequency components at these frequencies is compared with a limit value (decision box 38).

When the calculated value of these spectral components of the pressure signal for the frequencies of 6, 7, 8, 9 and 10 Hz exceed a limit value that may be set empirically, this is rated as muscular tremor of the patient (box 40). The instantaneously examined oscillation rated as having a muscular tremor of the patient superimposed thereon or as being caused by muscular tremor of the patient is disregarded or rejected.

Only such oscillations for which the sum of the values of the frequency components at 6, 7, 8, 9 and 10 Hz does not exceed the limit value, are admitted for further processing for determining the systolic, diastolic or mean blood pressure (box 42).

The aspect of the invention described in so far thus relates to the rejection of such oscillations that are impaired by artifacts caused by trembling of the patient or muscular tremor for instance due to undercooling of the patient.

As described hereinbefore, artifacts may also be caused by movements of the patient. In order to disregard oscillations that are caused by movements of the patient, additional processing is performed as shown in FIGS. 2 and 3.

Starting again on the basis of the pressure channel signal, a time window is defined by means of a timer within which the pressure channel signal is observed. This timer may be a timer for defining the time window that is also used for the discrete Fourier transform. The time window has a duration between 0.2 and 5 seconds, preferably 1 second. Within the time window (boxes 30, 32), the average value of the pressure channel signal is formed and subtracted from the signal. For determining a gradient of the resulting signal (box 40), which is freed from constant components, a straight line is applied to the signal according to the method of least error squares. Furthermore, the scatter of the signal within the time window is ascertained. In ascertaining the scatter, preferably the mean scatter is calculated, i.e. the mean value of the distance of the particular pressure signal curve point from the mean value thereof (box 44). It is also possible, but not necessary for the purposes of the invention, to calculate a standard deviation according to Gauss.

Next, it is determined whether the gradient and/or the scatter of the pressure channel signal (within the time window concerned) exceed predetermined limit values (decision boxes 42, 46). If this condition of examination is fulfilled, the conclusion is made that an artifact caused by movement of the patient is present, and the instantaneous oscillation under consideration is rejected or disregarded in further signal processing (box 50).

The evaluation of the remaining oscillations that are not impaired by an artifact is made, as described hereinbefore, by means of algorithms known per se, for deriving the diastolic, systolic or mean blood pressure value from the amplitude values or peak-to-peak values of the oscillations at the individual pressure steps (box 48).

In the above-described preferred embodiments, the cuff is firstly inflated to the predetermined pressure above the systolic pressure before stepwise reducing the pressure applied to the cuff and holding the pressure constant at each pressure step until either one oscillation caused by the heartbeat has occurred or until a predetermined time period has expired.

The principles of the invention equally apply to a method which derives the pressure samples by stepwise inflating the cuff and holding the pressure constant until at least one oscillation caused by the heartbeat has occurred or until a predetermined time period has expired while generating a pressure signal for this pressure step; i.e. a method which requires the stepwise inflating of the cuff for taking pressure signal samples rather than stepwise deflating the cuff as it has been described with reference to the preferred embodiment.

Similarly, the principles of the invention equally apply to a method for automatic non-invasive monitoring of the patient's blood pressure, wherein the pressure signals are obtained during the course of the continuous inflating of the cuff and/or during the course of the continuous deflating of the cuff.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

I claim:

1. A method for use in automatic non-invasive monitoring of a patient's blood pressure, wherein a cuff around an arm of the patient is inflated to a preselectd pressure so as to generate a pressure signal from an attached pressure sensor, the method comprising the steps of:

stepwise reducing a pressure applied to said cuff,
holding the applied pressure constant at each step until
   at least one oscillation caused by a heartbeat has occurred in said pressure signal, or until
   a preselectd time period has expired,
selecting at least one spectral component value of said at least one oscillation of the pressure signal in a frequency range between 6 and 10 Hz;
examining whether an amplitude of said selected spectral component value of said at least one oscillation in the frequency range between 6 and 10 Hz exceeds a limit value, and
if the limit is exceeded, disregarding said at least one oscillation of the pressure signal in further processing of said signal; or
if the limit is not exceeded, processing said at least one oscillation for use in determining a blood pressure parameter.

2. A method according to claim 1, wherein the determining step determines the spectral component of said at least one oscillation of the pressure signal in the frequency range between 6 and 10 Hz upon receiving a pressure channel signal produced by said pressure sensor, said pressure channel signal containing both oscillation components add constant components.

3. A method according to claim 2, further including deriving signals for use in determining a blood pressure parameter on the basis of an oscillation channel signal obtained by band-pass filtering of the pressure channel signal.

4. A method according to claim 2, further including deriving signals for use in determining a blood pressure parameter by employing an oscillation channel signal obtained by subtracting a mean value of the pressure channel signal from the pressure channel signal.

5. A method according to claim 1, wherein the selecting step performs a discrete Fourier transform to select the at least one spectral component value of the pressure signal in the frequency range between 6 and 10 Hz.

6. A method according to claim 1, wherein the selecting step performs a Fast Fourier transform to select the at least one spectral component of the pressure signal in the frequency range between 6 and 10 Hz.

7. A method according to claim 2, wherein the selecting step selects the at least one spectral component value of the pressure signal in the frequency range between 6 and 10 Hz, by observing a time window of the pressure channel with a duration between 0.2 and 5 seconds, and performing a discrete Fourier transform for plural frequencies between 6 and 10 Hz upon a signal resulting from a pressure channel signal after subtraction of a constant component.

8. A method for use in automatic non-invasive monitoring of a patient's blood pressure, wherein a cuff is applied around an arm of the patient, the cuff is inflated so as to generate a pressure signal from an attached pressure sensor, the method comprising the steps of:
   stepwise inflating said cuff to a preselectd pressure and holding an applied pressure constant at each step until
      at least one oscillation caused by a heartbeat has occurred in said pressure signal, or until
      a preselectd time period has expired,
   selecting at least one spectral component value of said at least one oscillation of said pressure signal in the frequency range between 6 and 10 Hz,
   examining whether the amplitude of said selected spectral component of said at least one oscillation in the frequency range between 6 and 10 Hz exceeds a limit value, and
      if the limit value is exceeded, disregarding the at least one oscillation of the pressure signal in further processing of said signal; or
      if the limit value is not exceeded, processing the at least one oscillation for use in determining a blood pressure parameter,
   after having reached the preselectd pressure, deflating said cuff.

9. A method according to claim 8, wherein the determining step selects the spectral component of the pressure signal in the frequency range between 6 and 10 Hz by employing a pressure channel signal produced by a pressure sensor, said pressure channel signal containing, in addition to oscillation components, also constant components.

10. A method according to claim 8, wherein the blood pressure parameter is one of systolic or diastolic or mean blood pressure and performing processing of the pressure signal by employing an oscillation channel signal obtained by band-pass filtering of the pressure channel signal or by subtracting the mean value of the pressure channel signal from the pressure channel signal.

11. A method according to claim 8, wherein the blood pressure parameter is one of systolic or diastolic or mean blood pressure and performing processing of the pressure signal by employing an oscillation channel signal obtained by subtracting the mean value of the pressure channel signal from the pressure channel signal.

12. A method according to claim 8, wherein the selecting step performs a discrete Fourier transform to select the at least one spectral component value of the pressure signal in the frequency range between 6 and 10 Hz.

13. A method according to claim 8, wherein the selecting step performs a fast Fourier transform to select the at least one spectral component of the pressure signal in the frequency range between 6 and 10 Hz.

14. A method according to claim 8, wherein the selecting step selects the at least one spectral component value of the pressure signal in the frequency range between 6 and 10 Hz, by observing a time window of the pressure channel with a duration between 0.2 and 5 seconds, and performing a discrete Fourier transform for several frequencies between 6 and 10 Hz upon a signal resulting from a pressure channel signal by subtraction of a constant component.

15. A method for use in automatic non-invasive monitoring of a patient's blood pressure, wherein a cuff is applied around an arm of the patient, the cuff is continuously inflated to a preselectd pressure or continuously deflated from a preselectd pressure so as to generate a pressure signal from an attached pressure sensor, the method comprising the steps of:
   selecting at least one spectral component value of an oscillation of the pressure signal in the frequency range between 6 and 10 Hz,
   examining whether an amplitude of the spectral component value exceeds a limit value, and
      if the limit is exceeded, disregarding the oscillation of the pressure signal in further processing of said signal; or
      if the limit is not exceeded, processing the oscillation for use in determining a blood pressure parameter.

16. A method according to claim 15, wherein the determining step determines the spectral component of the oscillation of the pressure signal in the frequency range between 6 and 10 Hz by employing a pressure channel signal containing both oscillation components and constant components.

17. A method according to claim 15, wherein the blood pressure parameter is one of systolic or diastolic or mean blood pressure and performing processing of the pressure signal by employing an oscillation channel signal obtained by band-pass filtering of a pressure channel signal or by subtracting the mean value of the pressure channel signal from the pressure channel signal.

18. A method according to claim 15, wherein the blood pressure parameter is one of systolic or diastolic or mean blood pressure and performing processing of the pressure signal by employing an oscillation channel signal obtained by subtracting the mean value of a pressure channel signal from the pressure channel signal.

19. A method according to claim 15, wherein the selecting step performs a discrete Fourier transform to select the at least one spectral component value of the pressure signal in the frequency range between 6 and 10 Hz.

20. A method according to claim 15, wherein the selecting step performs a Fast Fourier transform to select the at least one spectral component value of the pressure signal in the frequency range between 6 and 10 Hz.

21. A method according to claim 15, wherein the selecting step selects the at least one spectral component value of the pressure signal in the frequency range between 6 and 10 Hz, by observing a time window of the pressure channel with a duration between 0.2 and 5 seconds, and performing a discrete Fourier transform for several frequencies between 6 and 10 Hz upon a signal resulting from a pressure channel signal by subtraction of a constant component.

22. A blood pressure measuring apparatus for use in automatic noninvasive monitoring of a patient's blood pressure, said apparatus comprising:
   a cuff for application to an arm of a patient;
   a pump means for inflating said cuff to a preselectd pressure;

a pressure sensor coupled to said cuff for producing a pressure signal, valve means coupled to said cuff for stepwise reducing a pressure applied to said cuff and for holding an applied pressure constant at each step until at least one oscillation caused by a heartbeat has occurred in a pressure signal, or until a preselectd period of time has expired;

spectral component selecting means for selecting at least one spectral component value of the pressure signal in the 6 and 10 Hz frequency range;

processor means for examining whether an amplitude of the spectral component value exceeds a limit value, and if yes, disregarding an oscillation of the pressure signal; or if no, processing the oscillation for selecting either a systolic or a diastolic or a mean blood pressure.

23. A blood pressure measuring apparatus for use in automatic noninvasive monitoring of a patient's blood pressure, said apparatus comprising:

a cuff for application to an arm of the patient, a pressure sensor for producing a pressure signal, a pump means for stepwise inflating said cuff to a predetermined pressure and for holding an applied pressure constant at each step during inflation until at least one oscillation caused by a heartbeat has occurred in a pressure signal, or until a predetermined period of time has expired, a spectral component selecting means for determining at least one spectral component value of the pressure signal in a frequency range between 6 and 10 Hz, processor means for examining whether an amplitude of the spectral component value exceeds a limit value, and if yes, disregarding an oscillation of the pressure signal; or if no, processing the oscillation for determining a blood pressure parameter, valve means for deflating said cuff when a pressure applied to the cuff has reached the predetermined pressure.

24. A blood pressure measuring apparatus for use in automatic noninvasive monitoring of a patient's blood pressure, said apparatus comprising:

a cuff for application to an arm of the patient, pump means for continuously inflating said cuff to a predetermined pressure, a pressure sensor for producing a pressure signal during a course of continuously inflating said cuff to said predetermined pressure, a spectral component selecting means for determining at least one spectral component value of the pressure signal in a frequency range between 6 and 10 Hz, processor means for examining whether an amplitude of the spectral component value exceeds a limit value, and if yes, disregarding an oscillation including said one spectral component value of the pressure signal; or if no, processing the oscillation for selecting a blood pressure parameter, and valve means for deflating said cuff when a pressure applied to the cuff has reached the predetermined pressure.

25. A blood pressure measuring apparatus for use in automatic noninvasive monitoring of a patient's blood pressure, said apparatus comprising:

a cuff for application to an arm of the patient, pump means for inflating said cuff to a predetermined pressure, valve means for continuously deflating said cuff from said predetermined pressure, a pressure sensor for producing a pressure signal during a course of continuously deflating said cuff from said predetermined pressure, a spectral component selecting means for determining at least one spectral component value of the pressure signal in a frequency range between 6 and 10 Hz, processor means for examining whether an amplitude of the spectral component value exceeds a limit value, and if yes, disregarding an oscillation including said one spectral component value of the pressure signal; or if no, processing the oscillation for determining a blood pressure parameter.

* * * * *

UNITED STATES PATENT AND TRADEMARK OFFICE
CERTIFICATE OF CORRECTION

PATENT NO. : 5,427,109
DATED : June 27, 1995
INVENTOR(S) : Frankenreiter

It is certified that error appears in the above-indentified patent and that said Letters Patent is hereby corrected as shown below:

Claim 1, col. 12, line 28, change "preselectd" to —predetermined—.
Claim 2, col. 12, line 48, change "add" to —and—.
Claim 6, col. 12, line 64, after "component" insert —value—.
Claim 8, col. 13, line 13, change "preselectd" to —predetermined—.
Claim 8, col. 13, line 23, after "component" insert —value—.
Claim 8, col. 13, line 32, change "preselectd" to —predetermined—.
Claim 13, col. 13, line 63, after "component" add —value—.
Claim 15, col. 14, line 9, change "selectd" to —predetermined—.
Claim 15, col. 14, line 10, change "selectd" to —predetermined—.
Claim 22, col. 14, line 67, change "selectd" to —predetermined—.

Signed and Sealed this

Sixteenth Day of January, 1996

Attest:

Attesting Officer

BRUCE LEHMAN

Commissioner of Patents and Trademarks